United States Patent [19]
Carrell et al.

[11] Patent Number: 5,082,674
[45] Date of Patent: Jan. 21, 1992

[54] FOOD PRODUCT

[75] Inventors: Rebecca S. Carrell, Cambridge, Great Britain; Wietse van Dijk, Klaaswaal, Netherlands; Mervyn R. Goddard, Rushden, Great Britain; John B. Hayes, Den Haag, Netherlands

[73] Assignee: Thomas J. Lipton Co., Division of Conopco, Inc., Englewood Cliffs, N.J.

[21] Appl. No.: 585,855

[22] Filed: Sep. 19, 1990

[30] Foreign Application Priority Data

Sep. 29, 1989 [NL] Netherlands .................... 8902419
Apr. 19, 1990 [GB] United Kingdom ............. 9008755

[51] Int. Cl.$^5$ ............................................ A23B 7/10
[52] U.S. Cl. ........................... 426/52; 426/589; 426/613; 426/654; 426/662; 426/573; 426/555; 426/605
[58] Field of Search ............... 426/662, 654, 589, 613, 426/52, 555, 573, 605

[56] References Cited

U.S. PATENT DOCUMENTS

| | | | |
|---|---|---|---|
| 3,260,606 | 7/1966 | Azuma | 426/614 |
| 3,652,397 | 3/1972 | Pardun | 426/662 |
| 3,920,857 | 11/1975 | Barker et al. | 426/662 |
| 4,034,124 | 7/1977 | van Dam | 426/662 |
| 4,478,866 | 10/1984 | Ohta et al. | 426/662 |
| 4,957,768 | 9/1990 | Dutilh | 426/662 |

FOREIGN PATENT DOCUMENTS

| | | | |
|---|---|---|---|
| 62-262998 | 11/1987 | Japan | 426/662 |
| 1525929 | 9/1978 | United Kingdom | 426/662 |

OTHER PUBLICATIONS

FS Pilot-Niro Atomizer-9 pages.

*Primary Examiner*—Jeanette Hunter
*Attorney, Agent, or Firm*—James J. Farrell

[57] ABSTRACT

A process for the manufacture of a lysophospholipoprotein (LPLP)-comprising foodstuff by incorporating dried LPLP or dried LPLP-comprising material, preferably having a moisture content of at most 10 wt %, at a level of 0.1-90 wt.% therein. The dried LPLP serves as a texture-modifying agent, a glossing agent, a freeze-thaw stabilizing agent, a heat-stabilizing agent and a syneresis-inhibiting agent.

6 Claims, No Drawings

FOOD PRODUCT

This invention relates to foodstuffs, ingredients for foodstuffs or animal feed comprising phospholipoprotein which has been modified with phospholipase A and to a process of preparing such foodstuffs, ingredients for foodstuffs, or animal feed, as well as to the use of dried phospholipoprotein which has been modified with phospholipase A in foodstuffs, ingredients for foodstuffs or animal feed.

It is known from British Patent Specification GB-B-1,525,929 (Unilever) to treat phospholipoproteins or phospholipoprotein comprising materials, such as egg yolk, whole egg, blood serum, wheat protein, soybean, and the like with phospholipase A. Phospholipase A is an enzyme which effects cleavage of the bond binding a fatty acid radical to the glycerol part of the phospholipid molecule, thereby replacing this fatty acid radical by a hydroxyl group. In the case of phospholipase $A_2$ the fatty acid radical in the 2-position of the glycerol part of the phospholipid molecule is selectively splitted off.

The phospholipase A is also active when the phospholipid is complexed with protein (and then called phospholipoprotein throughout this specification and the attached claims). After the treatment with the phospholipase a lyso-phospholipoprotein (hereinafter referred to as "LPLP") is formed, in which a lyso-phospholipid is complexed with a protein. In GB-B-1,525,929 the use of the LPLP comprising material as an emulsion stabilizer, particularly in oil-in-water emulsions, enabled the manufacture of sterilisable emulsions, which in practice turned out to be commercially very successful, because they had a long shelf life and an excellent creamy taste.

In Japanese Patent Application JP-A-62 262,998 (Q.P. Corp.) there has been described a process for the manufacture of lysolecithin having substantially no residual enzyme activity. In this process a natural phospholipid containing substance, such as egg yolk, soybean, crude lecithin, and the like, is treated with phospholipase $A_2$ so that the phospholipid is converted into lyso-phospholipid, after which the thus treated material is spray-dried or freeze-dried, taking care that the temperature of the product is at most about 60° C., until the moisture content is at most 10% by weight. Subsequently the lyso-phospholipid is extracted from the powder obtained by means of a polar solvent, like methanol or ethanol, after which the polar solvent is evaporated from the extract and the lyso-lecithin, which is substantially free of any residual enzyme activity, is obtained.

The aim of the process according to JP-A-62 262,998 clearly is to obtain a specific grade of lyso-lecithin and not to obtain a LPLP. It has been indicated that the lysolecithin finally obtained, having substantially no residual enzyme activity, may be used in foodstuffs, but this use was already known.

It has now been found that it is possible to dry LPLP or LPLP comprising material, preferably to a moisture content of at most 10% by weight using air inlet temperatures of above 200° C., preferably from 210°-240° C., and air outlet temperatures of 85° C. and higher, e.g. from 85° C. to 95° C., without dissociating the lyso-phospholipid-protein complex, which is surprising since the protecting influence of the water of hydration is rapidly diminishing upon drying the complex, certainly at these relatively high temperatures. It turned out that not only the excellent emulsion stabilizing effect of the LPLP was retained after drying, but that the dried LPLP (when incorporated into preferably dried foodstuffs) or LPLP comprising material additionally proved to be an excellent texture modifying agent upon its rehydration. Also the dried LPLP or LPLP comprising material upon incorporation into certain foodstuffs enabled the deletion of certain artificial food additives, such as for example the sequestering agents in creamers, thus enabling the manufacture of entirely natural foodstuffs. In other foodstuffs, like custards, the added dried LPLP or LPLP comprising material upon reconstitution surprisingly appeared to act as a glossing agent. Thus, by using the dried LPLP or LPLP comprising material in, preferably dried, particulate foodstuffs or ingredients for foodstuffs, it appeared that upon reconstitution with edible liquids like water, milk, fruit juices, bouillon, and the like, products were obtained with surprisingly improved properties. Hence an area of novel, preferably dried, foodstuffs has been disclosed by the present invention, which foodstuffs cannot only be used for human consumption, but also in animal feedstuffs, like for example calf milk replacer.

Therefore the present invention relates to a process for the manufacture of an LPLP-comprising foodstuff, which is characterized in that dried lyso-phospholipoprotein (LPLP) or dried LPLP-comprising material is incorporated therein. Preferably, the dried LPLP-comprising material has a moisture content of at most 10% by weight.

By "foodstuff" is understood throughout this specification and the attached claims any ingestible material which can be used as foodstuff, an animal feed, or as an ingredient for a foodstuff or animal feed.

Preferably, the dried LPLP or dried LPLP-comprising material is incorporated into dried foodstuffs or dried ingredients for foodstuffs.

In some instances the moisture content of the dried LPLP can be somewhat higher, for example about 12% by weight, if the dried LPLP is admixed with very dry foodstuffs or ingredients for foodstuffs, so that after moisture migration and equilibration the average moisture content of the final mixture is at most 10% by weight.

The present invention also relates to a process for the manufacture of an LPLP-comprising foodstuff, which is characterized in that the foodstuff is selected from the group consisting of sauces, spreads, mayonnaise, dressings, soups, bakery products, creamers, creamer-thickeners, ice cream, drinks, dairy products, desserts, sherbets, meals, and combinations thereof.

The present invention finally relates to the use of dry LPLP or dried LPLP-comprising materials, preferably having a moisture content of at most 10% by weight, as a texture-modifying agent, a glossing agent, a freeze-thaw stabilizing agent, a heat-stabilizing agent, or a syneresis-inhibiting agent in a foodstuff.

The enzyme phospholipase A is an enzyme which effects cleavage of the bond binding a fatty acid radical to the glycerol part of the phospholipid molecule.

Phospholipase $A_1$ cleaves the bond in the 1-position, phospholipase $A_2$ (which is preferred) cleaves the bond in the 2-position.

The expression "modified" applied to phospholipoprotein as used throughout this specification and the attached claims denotes any degree of conversion brought about by the action of phospholipase A.

A suitable source of phospholipase A is pancreatin, which is preferably heat-treated, preferably under acidic conditions. The heat treatment is carried out at a temperature of from 60° C. to 90° C. for 3-15 minutes, preferably at a pH value of from 4 to 6.5. The enzyme composition thus obtained is substantially free from enzymatic activity other than resulting from phospholipase A, which is remarkably stable under the conditions of the above treatment.

Another suitable source of phospholipase is Lecitase 10-L (Trade Mark), a commercial preparation of phospholipase $A_2$ ex Novo Industri A/S, Denmark.

Also kosher enzymes like those derived from snake venom or bee venom may be used.

The degree of conversion of modified phospholipoprotein is in the specification and the attached claims expressed as the percentage of converted phosphatidylcholine plus phosphatidylethanolamine based on the total amount of phosphatidylcholine plus phosphatidylethanolamine present before conversion. An easy method to obtain the figures required to compute this percentage is quantitative thin-layer chromatography. Another simple method of determining the degree of conversion is the modified titrimetric method of Dole for the determination of the released fatty acids (see V. P. Dole and H. Meinertz, J. Biol. Chem. 235 (1960) 2595-2599).

The degree of conversion is determined inter alia by the temperature and pH at which and the period of time during which incubation of the phospholipoprotein with phospholipase takes place, as well as by the concentration of the enzyme and the presence of activating agents, such as calcium ions, or deactivating agents, such as e.g. zinc ions and ethylene diamine tetraacetate, during the incubation. The modification can be carried out in any convenient manner know per se.

It has been found that the degree of conversion of the modified phospholipoprotein should be at least 10%. Preferred is a degree of conversion of from 40% to 100%, especially from 60% to 90%.

Examples of suitable materials containing phospholipoproteins are: yeast, casein, skim milk powder, blood serum, egg yolk, whole egg, butter milk, whey, cream, soybean and wheat proteins, but also other phospholipoprotein-containing materials such, as plants and micro-organisms, may be used. The use of egg yolk and whole egg is preferred. The cholesterol content of the egg material can previously at least be reduced, e.g. by solvent extraction.

The source material of the phospholipoprotein can be subjected as such to the action of phospholipase A, but it is also possible to first isolate the phospholipoprotein from its source material and then subject this isolated phospholipoprotein to the action of phospholipase A. Preferably almost all of the phospholipoprotein in the source material is modified with the phospholipase A before the material is dried. Preferably, the phospholipase A is phospholipase $A_2$.

The modified phospholipoprotein (or LPLP) or LPLP comprising material is preferably dried by spray drying, taking care that the powder temperature does not exceed 75° C., preferably 65° C. Preferably, air inlet temperatures of from 210° C. to 240° C. and air outlet temperatures of from 85° C. to 95 C are used. The use of a spray-drying equipment provided with a fluidized bed, for example the FSD spray drayer (Trade Mark, ex A/S Niro Atomizer, Denmark) is preferred. The drying of the LPLP or LPLP comprising material may also be effected by freeze drying, however. After drying, the moisture content is preferably at most 10% by weight, and more preferably at most 5% by weight. The particulate material thus obtained has a relatively long shelf life and may be admixed with any other, preferably dried foodstuff material. Under certain conditions, i.e., when the foodstuff material with which the dried LPLP or LPLP-comprising material has to be admixed has a very low moisture content, the moisture content of the dried LPLP may be higher up to 15% by weight), because during the mixing of all the ingredients or thereafter, moisture migration takes place and the average moisture content of the final mixture will be lower, but should after equilibration preferably not be higher than 10% by weight. At higher moisture contents the chance of bacterial contamination upon storage increases, which is less desirable.

It is also possibly to dry, preferably by spray-drying, all the ingredients of the final product together with the LPLP or the LPLP comprising material, so as to arrive at a dried particulate foodstuff with an average moisture content of preferably at most 10% by weight. Also a number (or one) of the ingredients of the final food product may be dried together and thereafter mixed with the remainder of the dried, particulate ingredients, during which process the LPLP or LPLP comprising material may be present in the one part or in the other.

The dried, particulate LPLP or LPLP comprising material can be used in a very wide range of food products, particularly in those which are of the so-called dry mix-type. The amount of dried LPLP or LPLP comprising material in the food product can vary within wide ranges, e.g. from 0.1% to 90% by weight based on the total composition.

For dried sauce-, spread-, mayonnaise- and dressing-like food products for example, the amount of dried LPLP or LPLP comprising material in the final dried product may be from 0.1% to 20% by weight based on the total composition, preferably from 5% to 15% by weight, based on the total composition.

For dried bakery mixes, like cake mixes or pancake mixes, the amount of dried LPLP or LPLP comprising material in the final dried food product may range from 0.1% to 15% by weight, preferably from 5% to 10% by weight, based on the total composition.

In non-dairy creamers and creamer-thickeners the amount of dried LPLP or LPLP comprising material in the final product may range from 0.5% to 15% by weight, preferably from 1% to 10% by weight, based on the total composition.

In products like baked custard, the amount of dried LPLP or LPLP comprising material in the dried product may range from 0.5% to 20% by weight or higher, preferably from 10% to 20% by weight, based on the total composition.

In typical egg products the amount of dried LPLP or LPLP comprising material may be as high as up to 90% by weight, or sometimes even more.

The dry, particulate dressing-, sauce-, spread- and mayonnaise-type products according to the present invention may comprise spray drying aids (like maltodextrins), oils, fats (like for instance butter fat), oil or fat fractions, liquid or solid low-calorie non-digestible fat replacers (like the edible polyesters of polyhydric alcohols having at least four free hydroxyl groups, such as polyglycerols, sugars, or sugar alcohols, and saturated or unsaturated, straight or branched alkyl chain C8-C24 fatty acids, in which polyesters on an average at least 70% of the polyhydric alcohol hydroxyl groups have been esterified with the fatty acids), herbs, spices, pH regulating substances (like vinegar), flavouring agents, colouring agents (like beta-carotene), vitamins, antioxidants, thickening agents, sweetening agents, salt, vegetable particles, meat particles, emulsifiers, gums and stabilizers, preservatives, and the like and mixtures of these substances.

These dried particulate products can be reconstituted with edible liquids like milk, water, fruit juices, bouillons, wine and mixtures thereof.

It has been found that these dry, particulate dressing-, sauce-, spread- and mayonnaise-type products comprising dried LPLP or LPLP comprising material upon reconstitution give products with an excellent texture, taste and appearance, and which are retortable and exhibit a surprisingly good freeze/thaw stability. The products may be packaged in single serving packaging, but may also be supplied in larger quantities e.g. for catering purposes.

The dried modified phospholipoprotein (or dried LPLP) or dried LPLP comprising material may also be used in bakery mixes, preferably dry, particulate bakery mixes, like cake mixes, pan cake mixes and mixes for the preparation of pastries, cookies, muffins and rolls, and the like products. In the manufacture of these mixes it may be advantageous to spray dry the LPLP or LPLP comprising material on flour as a carrier material. These dry, particulate mixes may also comprise flour, leavening agents, sweetening agents, flavouring agents, emulsifiers, salt, proteins, antioxidants, vitamins, preservatives, fibres, fats, oils, oil or fat fractions, liquid or solid low-calorie non-digestible fat replacers as those described herebefore, and mixtures of these substances.

It has been found that the use of dried LPLP or LPLP-comprising material in dry particulate cake mixes upon reconstitution and baking leads to cakes with a very open, moist texture with excellent taste.

The dried modified phospholipoproteins (or dried LPLP) or dried LPLP comprising material may also be used in pudding mixes, custards, sherbet type products and ice cream mixes and frozen desserts such as ice milks and mellorines, further in scrambled egg and omelette mixes, Yorkshire pudding, but also in creamy drinks, such as yoghurt drinks, egg nog drinks, and the like. It has been found that in dry custard mixes the use of the dried LPLP or LPLP comprising material not only led to a very rich creamy texture upon reconstitution, but that it also acted as a glossing agent, imparting a shiny surface of the reconstituted product.

The invention is now illustrated on hand of the following examples which in no way are to be construed as limiting the scope of the present invention.

EXAMPLE I

Unto 890 grams of fresh egg yolk were added 25 mg of Lecitase 10-L (Trade Mark; a phospholipase $A_2$ preparation from porcine pancreatic glands having an activity of 10,000 International Units per ml, ex Novo Industri A/S, Denmark) whilst stirring gently. The mixture obtained was incubated for 4.5 hours at 54° C., after which the modified egg yolk was cooled to room temperature and any lumps were dispersed. The degree of conversion was 86%.

The modified egg yolk comprising LPLP was then spray-dried in a Niro spray-drier, Type: Production Minor (ex A/S Niro Atomizer, Denmark) using an air inlet temperature of 200° C. and an air outlet temperature of 75° C., so that a powder temperature of 40° C. was reached. A finely divided powder of LPLP comprising material a moisture content of 1.0 % by weight was obtained.

The spray-dried LPLP comprising material was used to prepare a dry particulate cake mix, using the following ingredients:

| | |
|---|---|
| Wheat flour[1] | 65.0 grams |
| Spray-dried egg white | 6.5 grams |
| Cocoa powder | 10.0 grams |
| Baking powder[2] | 5.0 grams |
| Spray-dried butter | 75.0 grams |
| Sugar | 75.0 grams |
| Spray-dried LPLP comprising material | 14.5 grams |

[1] Mc Dougalls Supreme Self Raising Flour
[2] A commercial sodium bicarbonate/edible acid-based baking powder The ingredients were mixed in dry, particulate form using a ribbon mixer. The obtained cake mix could be reconstituted by adding water in a weight ratio of 1 pbw of water to 3.14 pbw of dry particulate mix, whilst stirring gently. The obtained smooth batter was poured into a greased baking tin and placed into a preheated oven (180° C.) for 35-40 minutes.

The cake produced had a very open moist texture and was of excellent taste. The structure was different of that of a conventional cake prepared without the use of the LPLP in that the pores were greater.

EXAMPLE II

The spray-dried LPLP comprising material obtained in Example I was used to prepare a pancake mix using the following ingredients:

| | |
|---|---|
| Dried LPLP comprising material | 9.12 grams |
| Plain flour | 113.4 grams |

The dry particulate mixture obtained could be reconstituted into a smooth batter by mixing the total amount obtained with 284.0 grams of water or milk. Pancakes prepared from the batter had a slightly better taste than those prepared without the use of the dried LPLP comprising material.

EXAMPLE III

Egg yolk was treated in the same way as described in Example I, with the exception that the incubation time was 4 hrs at 55.5° C. after which the egg yolk was stored overnight at 5.5° C. and subsequently spray-dried in a FSD spray-drier (Trade Mark; ex A/S Niro Atomizer, Denmark) using an air inlet temperature of 210° C., an outlet air temperature of 82° C., so that the powder temperature was 50° C. A finely divided LPLP comprising material with a degree of conversion of 85% and a moisture content of 1.8% by weight was obtained.

The dried LPLP comprising material was used in the preparation of a dry mix for baked custard by dry mixing the following ingredients:

| | |
|---|---|
| Spray-dried LPLP comprising material | 20 grams |
| Spray-dried egg white | 12 grams |
| Granulated sugar (sucrose) | 60 grams |
| Skimmed milk powder | 50 grams |

The dry mixture obtained was reconstituted with water in a weight ratio of 1 pbw of dry mixture to 3 pbw of water by slowly adding the water to the powder whilst stirring. The obtained slurry was poured into a baking dish and baked in the oven for 25-30 minutes at 190° C.

A baked custard was obtained which with respect to colour, texture and flavour was superior to a traditionally prepared custard without using the LPLP comprising material of the same recipe. Moreover the baked custard comprising the LPLP immediately set upon cooling, and exhibited less syneresis than the traditional baked custard prepared with non-modified egg material.

EXAMPLE IV

The spray-dried LPLP comprising material obtained in Example III was used to prepare a dry stove top custard mix using the following ingredients:

| | |
|---|---|
| Spray-dried LPLP comprising material | 18 grams |
| Corn flour | 28 grams |
| Granulated sugar | 15 grams |
| Vanilla essence | 0.5 grams |

The dry mixture was reconstituted with whole milk in a weight ratio of 1 pbw of dry mix to 9.16 pbw of whole milk by slowly adding the milk to the dry mix while stirring in a saucepan. The mixture was brought to the boil while stirring continuously, was left to simmer for a few minutes and then removed from the heat. A stove top custard was obtained with a very rich creamy texture with a glossy surface. A stove top custard of the same recipe without the use of LPLP had a rather "gluggy" texture and not the excellent glossy surface. The dry stove top custard mix could also be adapted to give a number of other sweet cream sauces, such as brandy and butter scotch sauce.

EXAMPLE V

The spray-dried LPLP comprising material obtained in Example III was used to prepare a creme caramel mix using the following ingredients:

| | |
|---|---|
| Castor sugar | 53.25 grams |
| Spray-dried LPLP comprising material | 18.24 grams |
| Skimmed milk powder | 28.50 grams |
| Granulated sugar (sucrose) | 27.00 grams |
| Spray-dried egg white | 2,81 grams |

The dry mix with the exception of the which was packaged separately, could easily be converted into a creme caramel. The castor sugar was molten without stirring and once it was molten it was occasionally stirred until the colour was a golden brown. The melt was poured into bowls. Then water in a weight ratio of 1 pbw of the dry mixture without the castor sugar to 3.71 pbw of water was boiled and added to the remainder of the mix (without the castor sugar) while thoroughly stirring. The mixture obtained was poured into the bowls, placed in a bain-marie and cooked in a moderate oven (175° C.) for about 20 minutes, or until set. The product was then taken out of the oven, left to cool and turned out.

The obtained creme caramel had a very light open texture and the taste and texture were vastly superior to those of a creme caramel made with ordinary egg yolk, using the same recipe. Also the creme caramel made with the LPLP exhibited a quicker setting and showed less syneresis than the same product, prepared with ordinary egg yolk.

EXAMPLE VI

The spray-dried LPLP comprising material obtained in Example I was used to prepare a dry quiche filling mass, using the following ingredients:

| | |
|---|---|
| Spray-dried LPLP comprising material | 9.12 grams |
| Spray-dried egg white | 2.82 grams |
| Skimmed milk powder | 28.5 grams |
| Freeze-dried mushroom slices | 5.0 grams |

The dry mix obtained was reconstituted with water in a weight ratio of 1 pbw of dry mix to 6.34 pbw of water, by adding the water to the dry mix while beating. The obtained batter was poured into a flan dish and cooked for 20-25 minutes at 190° C. The appearance and the texture of the quiche obtained was superior to quiches of the same recipe prepared by using ordinary egg yolk.

EXAMPLE VII

The modified egg yolk obtained in Example I was mixed before it was spray-dried with the following ingredients:

| | |
|---|---|
| Modified egg yolk | 16.5 grams |
| Unsalted butter | 48.6 grams |
| Maltodextrin[1] | 10.3 grams |
| Water | 24.2 grams |

[1]Having a D.E. of 18-20

The water and the maltodextrin were heated while stirring to 60°-70° C., after which the modified egg yolk was added to the obtained solution. The butter was molten at the same time to 60°-70° C. The modified egg yolk and the maltodextrin solution were mixed in a Silverson mixer, after which the molten butter was added to obtain a coarse emulsion. The obtained emulsion was subsequently homogenised at a pressure of 2500-3000 psi (170 to 204 bar) in a Crepaco homogenizer. The homogenized emulsion was subsequently spray-dried, using the same spray-drier as in Example I, at an air inlet temperature of 200° C. and an air outlet temperature of 75° C.-90° C. A spray-dried Hollandaise sauce powder was obtained, having a moisture content of 1.1% by weight.

The obtained dry mixture was reconstituted in a weight ratio of 100 grams of dry mix to 6 grams of lemon juice, 28 grams of white wine and 20 grams of water to yield a very good Hollandaise sauce with excellent texture and appearance. The reconstituted Hollandaise sauce could be retorted for 20 minutes at 121° C and had an excellent freeze/thaw stability. It could be blast frozen to −30° C. and subsequently thawn to +15° C. without impairing the excellent texture and appearance. It also appeared possible to admix wine and vinegar powder, so that the dry mixture only needed to be reconstituted with water. The Hollandaise sauce could be varied in recipe to convert it into a Bearnaise sauce mix without difficulty and without impairing its qualities in any way. This example clearly shows that the modified phospholipoprotein material can also be spray-dried together with the other ingredients of the mixture to obtain the desired dry mix.

EXAMPLE VIII

The modified egg yolk obtained in Example III before it was spray-dried was mixed with the following ingredients:

| | |
|---|---|
| Sunflower oil | 51.3 grams |
| Modified egg yolk | 15.4 grams |
| Mustard | 0.8 grams |
| Sodium chloride | 0.8 grams |
| Distilled malt vinegar | 4.8 grams |
| Maltodextrin[1] | 3.5 grams |
| Water | 23.4 grams |

[1]Having a D.E. of 18-20

The water was heated to 60°-70° C., after which the other ingredients, with the exception of the oil, were dispersed therein using a Silverson-mixer. Finally the oil was slowly added to the dispersion. The obtained emulsion was homogenized at a pressure of 2500-3000 psi (170 to 204 bar) in a Crepaco homogenizer. The homogenized emulsion was spray-dried, using the same spray-drier as in Example I, at an air inlet temperature of 200° C. and an air outlet temperature of 75°-90° C. A spray-dried mayonnaise powder was obtained, having a moisture content of 1.0% by weight.

The dried mayonnaise could be readily reconstituted with water in a ratio of 100 grams of dry mixture and 25 ml of water to yield a very high quality mayonnaise, which was retortable.

EXAMPLE IX

In this Example a number of non-dairy creamers was prepared, using a vegetable fat, modified egg yolk and a carrier material (maltodextrin) for the spray-drying. In three experiments the amount of modified egg yolk, as obtained in Example I, was varied from 2.5% to 5.0% to 7.5% by weight, based on the final dry composition. In the spray-drying experiments, the maltodextrin (having a D.E. of 18-20) together with the modified egg yolk was dissolved in water of 60°-70° C. Separately the fat was heated to the same temperature of 60° C.-70° C. and this heated fat was mixed with the maltodextrin solution in a Silverson mixer by slowly adding the heated fat to the solution while mixing. The coarse emulsion obtained was homogenized in a Crepaco homogeniser at a pressure of 2500-3000 psi (170 to 204 bar).

The homogenised emulsion was spray-dried in the same apparatus as used in Example I, using an air inlet temperature of 200 C and an air outlet temperature of 75° C.-90° C. The recipes (on a dry basis in percent by weight) were as follows:

| | (a) | (b) | (c) | (d) |
|---|---|---|---|---|
| Vegetable fat[1] | 35% | 35% | 35% | 50% |
| Modified egg yolk | 2.5% | 5.0% | 7.5% | 7.2% |
| Maltodextrin | 62.5% | 60.0% | 57.5% | 42.8% |

[1]A hardened palm oil with melting point of 40° C.

In all instances a spray-dried creamer powder was obtained having a moisture content of 0.6% by weight, which could easily be reconstituted with water. It appeared also that the higher the level of modified egg yolk, the whiter the resultant particulate product was. The great advantage of this product is that no artificial ingredients are present (there is no need to use emulsifiers, sequestering agents like citrates and phosphates and caseinate). Moreover the absence of caseinate makes it possible to use these creamers in a rather acid environment, like for instance cream-style tomato soup and hence the present invention provides a new class of non-dairy creamers with superior properties compared to the non-dairy creamers with caseinate. Moreover it was found that the creamers according to the invention had an enhanced heat stability and exhibited a thickening effect by providing some viscosity to the environment in which they are used.

Thus with one formulation more than one very advantageous properties are added to the foodstuff. It appeared that particularly in instant sauces and gravy-like products these pronounced properties led to very high quality products. The creamers were also applied in dips, like e.g. an onion dip and in creamy drinks, like e.g. yoghurt based drink.

The dried particulate creamer prepared above as recipe (c) was used in a cream of mushroom soup formulation (expressed in grams/cup):

| | |
|---|---|
| Modified egg yolk based creamer | 11.35 grams |
| Corn flour | 8.33 grams |
| Spray-dried mushroom extract | 3.18 grams |
| Sodium chloride | 1.51 grams |
| Flavourings | 0.32 grams |
| Maltodextrin (D.E. = 18-20) | 1.52 grams |

The dry mixture could be reconstituted with 180 ml of boiling water to a cream of mushroom soup of excellent texture and taste.

The dried, particulate creamer as prepared according to recipe (b) above was used in a dry sauce mix of the following composition (expressed in grams/cup):

| | |
|---|---|
| Modified egg yolk based creamer | 9.88 grams |
| Dried potato starch | 16.12 grams |
| Salt | 1.00 grams |
| Spray-dried mushroom extract | 4.00 grams |
| Flavouring agents | 3.18 grams |

The total amount of this dry particulate mixture could be reconstituted by stirring it with 200 ml of water yielding a sauce a very good texture and viscosity.

The dried particulate creamer prepared above as recipe (a) was also used in a cream of tomato soup formulation (expressed in grams/cup):

| | |
|---|---|
| Modified egg yolk based creamer | 10.00 grams |
| Tomato powder | 6.00 grams |
| Granulated sugar | 4.74 grams |
| Granulated corn flour | 5.03 grams |
| Maltodextrin (D.E. = 18-20) | 2.00 grams |
| Sodium chloride | 1.34 grams |

The dry mixture could be reconstituted with 180 ml of boiling water to a cream of tomato soup of pH=4.2, having an excellent texture and taste.

This soup was in reconstituted form also canned and then retorted for 20 minutes at 121° C. The excellent creaminess of the soup was not impaired during this retorting.

EXAMPLE X

In the same way as described in Example IX a non-dairy creamer was prepared, using the following ingredients:

| | |
|---|---|
| Low-calorie solid fat replacer[1] | 35% by weight |
| Modified egg yolk[2] | 2% by weight |
| Maltodextrin (D.E. = 18-20) | 63% by weight |

[1] A sugar polyester having an octa-ester content of 80-85%, prepared from a mixture of 55 wt. % fully hardened soybean oil fatty acids and 45 wt % of slightly hardened soybean oil fatty acids, with a hydroxyl number of 4.1 and a melting point of 42° C.
[2] According to Example I.

A dried, particulate creamer, having the same excellent properties as those prepared in Example IX, was obtained. This creamer could advantageously be used in dry cream-style soup and sauce mixes.

EXAMPLE XI

A creamer-thickener was prepared using the following ingredients:

| | |
|---|---|
| Modified egg yolk (according to Example I) | 41.25 grams |
| Vegetable fat[1] | 288.75 grams |
| Maltodextrin (D.E. = 18-20) | 226.50 grams |
| Dried potato starch | 313.50 grams |
| Water | 630.00 grams |

[1] A hardened palm oil with melting point of 40° C.

The modified egg yolk was dissolved in water with the maltodextrin and heated to 60°-70° C.; the fat was molten to a similar temperature and mixed into the water phase using a Silverson mixer to obtain a coarse emulsion. This emulsion was homogenised in a Crepaco homogeniser at a pressure of 2550-3000 psi (170 to 204 bar).

The homogenised emulsion was spray-dried in the same apparatus as used in Example I, using an air inlet temperature of 200° C. and an air outlet temperature of 75° C.-90° C. A dry powder with a moisture content of 0.9% by weight was obtained.

The dried, particulate creamer thickener, prepared above, was used in a cream of mushroom soup formulation (expressed in grams per cup):

| | |
|---|---|
| Creamer-thickener | 11.00 grams |
| Spray-dried mushroom extract | 3.18 grams |
| Maltodextrin (D.E.= 18-20) | 1.52 grams |
| Sodium chloride | 1.51 grams |
| Flavouring agent | 0.32 grams |

The dry mixture could be reconstituted with 180 ml of boiling water to a cream of mushroom soup of excellent taste and texture.

The same dried particulate creamer-thickener, prepared above, was used in a creamy tomato sauce mixture of the following recipe:

| | |
|---|---|
| Creamer-thickener | 20.0 grams |
| Tomato powder | 20.0 grams |
| Granulated sugar | 4.74 grams |
| Maltodextrin (D.E. = 18-20) | 2.0 grams |
| Sodium chloride | 1.34 grams |

The particulate composition was reconstituted with 200 ml of boiling water to a creamy tomato sauce of pH=4.3. This sauce could be retorted at 121° C. for 20 minutes without any visible effect and without impairing its taste.

EXAMPLE XII

The dried LPLP comprising material prepared in Example III was used to prepare a warm custard using the following ingredients:

| | |
|---|---|
| Spray-dried LPLP comprising material according to Example III | 18.24 grams |
| Skimmed milk powder | 57.00 grams |
| Granulated corn flour | 40.00 grams |
| Sugar | 15.00 grams |

All the ingredients were weighed out and placed in a bowl, after which one pint of boiling water was mixed in, whisking continuously. After this two tea spoons of brandy were stirred in. A brandy sauce of rich texture and excellent taste was obtained.

EXAMPLE XIII

A dry mix for the preparation of ice cream was prepared from:

| | |
|---|---|
| Skimmed milk powder | 9.4 grams |
| Granulated sugar | 49.9 grams |
| Spray-dried fat powder with 50% by weight of fat | 28.1 grams |
| Spray-dried LPLP comprising | 12.5 grams |

For every 100 grams of this dry mixture, 200 ml of cold water were added and the obtained mixture was well dispersed using a hand whisk. After this the mixture was chilled in a domestic refrigerator at 5° C. for 2 hours. Hereafter the mixture was whisked again and subsequently frozen in a domestic freezer at −20° C. until the mixture was entirely frozen. The ice-cream obtained had a rich, smooth, creamy texture without the large ice crystals often associated with ice-cream obtained from dry mixes for ice-cream. Upon the addition of a foaming agent a still lighter texture was obtained.

EXAMPLE XIV

Non-pasteurized egg yolk comprising 7% by weight of sodium chloride and 1% by weight of potassium sorbate was treated for 4 hours with 50 mg/kg of egg yolk of the enzyme Lecitase 10L (Trade Mark, ex Novo Industri A/S. Denmark, strength 10,000 International Units per ml) at 55.5° C. During this treatment, the mixture was stirred for 30 seconds during each 3 minutes.

The egg yolk thus treated was fed at a rate of 25 kg/h to a Niro FSD spray dryer (ex A/S Niro Atomizer, Denmark). The temperature of the inlet air was 210° C., the temperature of the outlet air was 85° C. The temperature at the inlet of the fluidized bed was 40° C. and the powder temperature was 35° C. The pressure drop over the fluidized bed was 48 mm water column. The atomizer slit determining the spray angle in the dryer was set at −2.2 mm.

A dry powder was obtained at a rate of 12.25 kg/h having a moisture content of 1.8% by weight.

A microbiological investigation showed that the powder obtained had a germ count of less than 10.

The dry powder obtained was used for the preparation of a mayonnaise. 7.4 g of the dry powder were mixed with 22.2 g of water to form a slurry and to this slurry were added: 2.0 g of common salt, 3.0 g of sugar, 1.0 g of citric acid, 1.4 g of starch and 1 g of herbs. The L slurry thus obtained was heated to 60°–64° C. for 2–2.5 minutes and subsequently cooled to room temperature. Then 12.0 g of vinegar and 150.0 g of soybean oil were stirred in and the mixture obtained was homogenized at room temperature. A pasteurizable and sterilizable, creamy mayonnaise with excellent organoleptic properties was obtained.

EXAMPLE XV

Non-pasteurized egg yolk comprising 7% by weight of common salt and 1% by weight of potassium sorbate was treated with Lecitase 10L as described in Example XIV. The product thus treated was subsequently pasteurized by heating in a scraped surface heat exchanger for 30 seconds at a temperature of 65.5°–75.5° C. The treated product thus pasteurized was fed at a rate of 25 kg/h to a Niro FSD spray dryer at a product temperature of 8° C.–15° C. The inlet air temperature was 240° C., the outlet air temperature was 95° C., the temperature at the inlet of the fluidized bed was 60° C. and the powder temperature was 50° C. The pressure drop over the fluidized bed was 40 mm of water column. The atomizer slit determining the spray angle in the dryer was adjusted to −2.0 mm.

A dry powder was obtained at a rate of 12.5 kg/h having a moisture content of 2.0% by weight and a germ count of 10.

EXAMPLE XVI

In the same way as described in Example XIV, egg yolk was treated with Lecitase 10L, after which the treated egg yolk was dried in the same dryer was described in Example XIV, under the following conditions : inlet air temperature 210° C.; outlet air temperature 92° C.; temperature at the inlet of the fluidized bed 40° C.; powder temperature 42.5° C.; pressure drop over the fluidized bed 40 mm water column; adjustment of atomizer slit −2.0 mm. A dry powder was obtained at a rate of 12.0 kg/h having a moisture content of 1.8% by weight and a germ count of 20.

We claim:

1. A process for the manufacture of a lyso-phospholipoprotein (LPLP)-comprising, dried particulate foodstuff, which comprises incorporating into the foodstuff from 0.1% to 90% by weight of the foodstuff of dried LPLP or dried LPLP-comprising material, obtained by:
   (a) treating phospholipoprotein (PLP) or PLP-comprising material with phospholipase A such that the percentage of converted phosphatidylcholine plus phosphatidylethanolamine based on the total amount of phosphatidylcholine plus phosphatidylethanolamine present before conversion is at least 10% and spray-drying the thus treated material at an air inlet temperature of from 200° C. to 240° C. and an air inlet temperature of from 75° C. to 95° C., so as to reach a final moisture temperature of at most 10% by weight.

2. A process according to claim 1, wherein in step (a) the percentage of converted phosphatidylcholine plus phosphatidylethanolamine based on the total amount of phosphatidylcholine plus phosphatidylethanolamine present before conversion is from 40% to 100%.

3. A process according to claim 1 wherein the LPLP is derived from whole egg or egg yolk.

4. A dried, particulate foodstuff comprising from 0.1% to 90% by weight of dried lyso-phospholipoprotein (LPLP) or dried LPLP-comprising material, obtained by:
   (a) treating phospholipoprotein (PLP) or PLP-comprising material with phospholipase A such that the percentage of converted phosphatidylcholine plus phosphatidylethanolamine based on the total amount of phosphatidylcholine plus phosphatidylethanolamine present before conversion is at least 10%, and
   (b) spray-drying the thus treated material at an air inlet temperature of from 200° C. to 240° C. and an air inlet temperature of from 75° C. to 95° C., so as to reach a final moisture content of at most 10% by weight.

5. A foodstuff according to claim 4, wherein in step (a) the percentage of converted phosphatidylcholine plus phosphatidylethanolamine based on the total amount of phosphatidylcholine plus phosphatidylethanolamine present before conversion is from 40% to 100%.

6. A foodstuff according to claim 4, wherein the LPLP is derived from whole egg or egg yolk.

* * * * *

UNITED STATES PATENT AND TRADEMARK OFFICE
CERTIFICATE OF CORRECTION

PATENT NO. : 5,082,674

DATED : January 21, 1992

INVENTOR(S) : Carrell et al.

It is certified that error appears in the above-identified patent and that said Letters Patent is hereby corrected as shown below:

In Claim 1, second to last line, change the word "temperature" to the word -- content --.

Signed and Sealed this

Twenty-seventh Day of April, 1993

Attest:

MICHAEL K. KIRK

Attesting Officer

Acting Commissioner of Patents and Trademarks